United States Patent [19]

Buysch et al.

[11] Patent Number: 6,001,768

[45] Date of Patent: Dec. 14, 1999

[54] SUPPORTED CATALYSTS CONTAINING A PLATINUM METAL AND PROCESS FOR PREPARING DIARYL CARBONATES

[75] Inventors: Hans-Josef Buysch; Carsten Hesse, both of Krefeld; Jörg-Dietrich Jentsch, Mülheim; Johann Rechner, Kempen; Eberhard Zirngiebl, Köln, all of Germany

[73] Assignee: Bayer Aktiengesellschaft, Leverkusen, Germany

[21] Appl. No.: 08/627,221

[22] Filed: Mar. 29, 1996

[30] Foreign Application Priority Data

Apr. 5, 1995 [DE] Germany ............................... 19512618

[51] Int. Cl.[6] ............................... B01J 27/13; B01J 23/00; C07C 69/96

[52] U.S. Cl. ..................... 502/230; 502/308; 502/309; 502/311; 502/318; 502/321; 502/324; 502/325; 502/326; 502/330; 502/331; 502/345; 502/350; 502/312; 502/313; 502/314; 502/315; 502/316; 558/270; 558/271; 558/274; 558/275

[58] Field of Search ................... 502/230, 308, 502/309, 311–316, 318, 321, 324, 325, 326, 330, 331, 345, 350; 558/270, 271, 274, 275

[56] References Cited

U.S. PATENT DOCUMENTS

| | | | |
|---|---|---|---|
| 4,039,572 | 8/1977 | Funakoshi et al. | 260/468 K |
| 5,231,213 | 7/1993 | Landscheidt et al. | 558/277 |
| 5,288,894 | 2/1994 | Landscheidt et al. | 558/277 |
| 5,322,965 | 6/1994 | Immel et al. | 564/446 |
| 5,473,094 | 12/1995 | Ooms et al. | 558/270 |
| 5,498,742 | 3/1996 | Buysch et al. | 558/274 |
| 5,498,744 | 3/1996 | Jenisch et al. | 558/277 |
| 5,502,232 | 3/1996 | Buysch et al. | 558/270 |
| 5,516,878 | 5/1996 | Sasaki et al. | 502/150 |
| 5,527,875 | 6/1996 | Yokoyama et al. | 528/196 |
| 5,527,942 | 6/1996 | Ooms et al. | 558/274 |

FOREIGN PATENT DOCUMENTS

| | | | |
|---|---|---|---|
| 0501265 | 9/1992 | European Pat. Off. | B01J 23/64 |
| 0503581 | 9/1992 | European Pat. Off. | C07C 68/00 |
| 0523508 | 1/1993 | European Pat. Off. | C07C 69/96 |
| 0538676 | 4/1993 | European Pat. Off. | C07C 68/00 |
| 0572980 | 8/1993 | European Pat. Off. | C07C 69/96 |
| 0614876 | 9/1994 | European Pat. Off. | C07C 68/00 |
| 0654461 | 5/1995 | European Pat. Off. | C07C 68/00 |
| 2815512 | 10/1979 | Germany | C07C 69/96 |
| 1165551 | 6/1989 | Japan . | |
| 4257546 | 9/1992 | Japan | C07C 69/96 |
| 4261142 | 9/1992 | Japan | C07C 69/96 |
| 1578713 | 11/1980 | United Kingdom | C07C 68/00 |

*Primary Examiner*—Mark L. Bell
*Assistant Examiner*—Patricia L. Hailey
*Attorney, Agent, or Firm*—Sprung Kramer Schaefer & Briscoe

[57] ABSTRACT

In the process for preparing an aromatic carbonate from an aromatic hydroxy compound, CO and $O_2$ in the presence of a quaternary salt and a base, use is advantageously made of supported catalysts which, in the reaction-ready state, contain a platinum metal, a platinum metal compound or a complex containing a platinum metal compound on a support comprising a metal oxide whose metal can occur in a plurality of oxidation states.

20 Claims, No Drawings

SUPPORTED CATALYSTS CONTAINING A PLATINUM METAL AND PROCESS FOR PREPARING DIARYL CARBONATES

BACKGROUND OF THE INVENTION

1. Field of the Invention

The present invention relates to supported catalysts containing a platinum metal and their use in processes for preparing diaryl carbonates by reaction of aromatic hydroxy compounds with carbon monoxide and oxygen, which are characterized in that pulverulent or shaped supports which can act as redox catalysts under reaction conditions are used.

2. Description of the Related Art

It is known that organic carbonates can be prepared by oxidative reaction of aromatic hydroxy compounds with carbon monoxide in the presence of a noble metal catalyst (German Offenlegungsschrift 28 15 512). The noble metal preferably used is palladium. In addition, a cocatalyst (e.g. manganese or cobalt salts), a base, a quaternary salt, various quinones or hydroquinones and desiccants can be used. The reaction can be carried out in a solvent, preferably methylene chloride.

For economically carrying out this process, not only the activity and the selectivity but also the effective recovery of the noble metal catalyst are of decisive importance: for one thing, the noble metal catalyst represents a considerable cost factor. Losses of noble metal catalyst have to be replaced at high cost. Furthermore, no residues of noble metal catalyst may remain in the product. For the process of oxidative carbonylation of aromatic hydroxy compounds to give diaryl carbonates, the economical and efficient recovery of homogeneous catalysts has hitherto not been described. A noble metal catalyst can be separated from a liquid reaction mixture with less effort, e.g. by filtration or centrifugation, if heterogeneous catalysts, e.g. supported catalysts, are used.

For preparing supported catalysts, generally suitable materials are known. Depending on the type of process, use is made of supports having a high internal surface area, for example alumina, magnesia, activated carbon or silica having more than 50 m² of surface area per gram, or supports having surface areas around 5 m²/g and correspondingly larger pore radii, for example carbon black, titanium dioxide, iron oxide or zinc oxide, or coarse-grained supports, for example silicon carbide and corundum (Ullmanns Enzyklopädie der technischen Chemie, 3rd edition, Berlin/Munich 1957, Volume 9, p. 263 ff.). Essentially, it is possible to use both synthetic materials such as activated aluminas, silica gels, silicates, titanium dioxides or activated carbons and also materials from natural sources, for example pumice, kaolin, bleaching earths, bauxites, bentonites, kieselguhr, asbestos or zeolites.

In EP 572 980, EP 503 581 and EP 614 876, use is made of supported noble metal catalysts containing 5% of palladium on carbon supports. However, according to our own studies, such supported catalysts give only very unsatisfactory conversions, if any, so that these too are not suitable for an economical process.

In JP 01/165 551 (cited according to C.A. 112 (1990), 76618j) it is mentioned that, for the preparation of aromatic carbonates, palladium or palladium compounds such as palladium acetylacetonate can be used in combination with alkali metal (alkaline earth metal) iodides or onium iodides such as tetrabutylammonium iodide and at least one zeolite.

JP 04/257 546 and JP 04/261 142 describe, in one example each, a supported catalyst for preparing aromatic carbonates in which granulated silicon carbide is used as support material for a supported catalyst in a distillation column. Although the relevant examples are carried out under drastic conditions (high pressure, high temperature), this catalyst makes possible only very low space-time yields. These low space-time yields make economical preparation of aromatic carbonates using such supported catalysts impossible.

Up to now, there has therefore been no supported catalyst available by means of which diaryl carbonates can be prepared economically and efficiently by reaction of an aromatic hydroxy compound with carbon monoxide and oxygen.

It was therefore an object of the invention to find a supported catalyst having high activity and selectivity which allows the economically efficient preparation of diaryl carbonates by reaction of an aromatic hydroxy compound with carbon monoxide and oxygen.

SUMMARY OF THE INVENTION

It has now been found that the above disadvantages can be overcome if use is made of supported platinum metal catalysts whose supports are transition metal oxides such as, for example, those of V, Mn, Ti, Cu, La, the rare earth metals and their mixtures. These transition metal oxides are, according to the invention, used as powder, pellets or binder-containing extrudates. Suitable binders are, for example, $SiO_2$, $Al_2O_3$ or clay minerals. The binder contents can be varied within a wide range, for example from 0.5 to 99.5% by weight, based on the total weight of the support. The supports of the invention are, according to previous conceptions, effective by acting together with the platinum metal compound like a separately added cocatalyst; however, all disadvantages of separately added cocatalysts are avoided, for instance the mixing with the reaction product and thus the contamination of the latter. In accordance with the conception mentioned, all the metals specified are ones which can occur in a plurality of oxidation states.

The supported catalysts of the invention contain, in the reaction-ready state, a platinum metal, a platinum metal compound or a complex containing a platinum metal compound in an amount of from 0.01 to 15% by weight, preferably from 0.05 to 10% by weight, calculated as the platinum metal and based on the total weight of the catalyst, on a support comprising one or more oxides of the metals Ti, V, Mn, Cr, Fe, Co, Ni, Cu, La, Nb, Mo, Pb, the rare earth metals having the atomic numbers from 58 to 71 and the actinides having the atomic numbers 89–92, preferably comprising one or more oxides of the metals Ti, V, Mn, Cr, Fe, Co, Ni, Cu, La, Nb, Mo, Pb, Ce, Pr, Nd, Sm, Eu, Gd, Th, Dy, Ho, Er, Tm, Yb, Lu and U.

The invention further provides a process for preparing an organic carbonate of the formula

R—O—CO—O—R (I)

where

R is substituted or unsubstituted $C_6$–$C_{12}$-aryl, preferably substituted or unsubstituted $C_6$-aryl, particularly preferably phenyl, by reaction of an aromatic hydroxy compound of the formula

R—O—H (II), where R is as defined above, with carbon monoxide and oxygen in the presence of a cocatalyst, a quaternary ammonium or phosphonium salt and a base at from 30 to 200° C., preferably from 30 to 150° C., particularly preferably from 40 to 120° C., and at a pressure of from 1 to 150 bar, preferably from 2 to 50 bar, particularly preferably from 5 to 25 bar, which is characterized in that the reaction is carried out in the presence of supported platinum metal catalysts of the above-described type.

DETAILED DESCRIPTION OF THE INVENTION

For the example of the formation of diphenyl carbonate, the reaction on which the process of the invention is based can be represented in terms of formulae as follows:

Catalyst supports suitable for use according to the invention are, inter alia, oxides of the following metals: Ti, V, Mn, Cr, Fe, Co, Ni, Cu, La, Nb, Mo, Pb, rare earth metals having the atomic numbers 58–71 and the actinides having the atomic numbers 89–92, both in the sense of chemically uniform pure substances and as mixtures. Oxides of La and the rare earth metals, in particular, are frequently obtainable as a mixture as they occur in association in nature, and can be used in this form. The metals on which the oxides are based can, in the form of their cations, assume at least 2 different valencies. Preferably, these are one or more metal oxides from the group Ti, V, Mn, Cr, Fe, Co, Ni, Cu, La, Nb, Mo, Pb, Ce, Pr, Nd, Sm, Eu, Gd, Tb, Dy, Ho, Er, Tm, Yb, Lu and U.

The oxides of V, Mn, Ti, Co, Cu, La, the rare earth metals (atomic numbers 58–71) and their mixtures have been found to be particularly suitable.

Catalyst supports used according to the invention can be prepared by precipitation of the desired metal oxide/hydroxide, washing the precipitate to remove inorganic by-products and drying.

If desired, dried catalyst supports can be further modified by extrudation, tabletting, optionally with mixing in of further catalyst supports or binders such as $SiO_2$ or $Al_2O_3$, and calcination. Preparation and further processing of the catalyst supports used according to the invention are well known to those skilled in the art and are prior art. Use of the above-described preparation methods gives porous solids insoluble in the reaction medium. Their composition varies because it depends on a wide variety of factors in the preparation conditions, such as temperature, concentration and nature of the reactants, rate and order of introduction of the reactants, pH during the preparation, duration of the precipitation, volume and pH of the washing solutions, duration and temperature of drying and calcination, etc. However, this varying composition of the metal oxides has little influence on their suitability as catalyst supports. $TiO_2$ supports can be used, for example, in the rutile, anatase or brookite form, preferably in the rutile form having internal surface areas of from 2 to 300 $m^2/g$, preferably from 5 to 200 $m^2/g$.

The support can be used as powder or as a shaped body. If the supported catalyst is arranged in a fixed bed, the support is preferably used as shaped bodies, e.g. as spheres, cylinders, rods, hollow cylinders, rings, etc.

The reactive component of the catalyst for the process of the invention is applied to the specified metal oxides as support. This reactive component comprises, in the reaction-ready state, a platinum metal, a platinum metal compound or a complex containing a platinum metal compound, preferably a platinum metal, a platinum metal halide or a complex containing a platinum metal halide, where the said complex can additionally contain, for example, olefins, amines, phosphines, nitriles, carbon monoxide or water, for example $A_2(PdHal_4)$, where A represents, for example, Li, Na, K, $NH_4$, Rb, Cs, $NR_4$, and R represents a $C_6$–$C_{10}$-aryl, $C_7$–$C_{12}$-aralkyl and/or $C_1$–$C_{20}$-alkyl radical and Hal represents a halogen such as, for example, F, Cl, Br, I. The platinum metal is present in an oxidation state of from 0 to 4.

Such complexes are basically known. Examples are: $Li_2(PdCl_4)$, $Na_2(PdCl_4)$, $K_2(PdCl_4)$, $(NBu_4)_2(PdCl_4)$, $Na_2(PdBr_4)$, $K_2(PdBr_4)$, $(NBu_4)_2(PdBr_4)$ where Bu=n-butyl; examples of olefin-containing platinum metal complexes are [allylpalladium chloride] dimer—$[C_3H_5PdCl]_2$, 1,5-cyclooctadienepalladium dichloride—$C_8H_5PdCl_2$; examples of phosphine-containing platinum metal complexes are [1,2-bis-(diphenylphosphino)ethane]palladium dichloride—$Pd[(C_6H_5)_2PCH_2CH_2P(C_6H_5)_2]Cl_2$, bis(triphenylphosphine)palladium dichloride—$Pd[P(C_6H_5)_3]_2Cl_2$; examples of amine-containing platinum metal complexes are diamminepalladium dibromide—$Pd(NH_3)_2Br_2$, diamminepalladium dichloride—$Pd(NH_3)_2Cl_2$, tetramminepalladium tetrachloropalladate—$[Pd(NH_3)_4][PdCl_4]$; examples of nitrile-containing platinum metal complexes are bis(acetonitrile)palladium dichloride—$Pd(CH_3CN)_2Cl_2$, bis(benzonitrile)palladium dichloride—$Pd(C_6H_5CN)_2Cl_2$; examples of carbon monoxide-containing platinum metal complexes are tetrabutylammonium tribromocarbonylpalladate —$(NBu_4)Pd(CO)Br_3$ (where Bu=n-butyl) and tetrabutylammonium trichlorocarbonylpalladate—$(NBu_4)Pd(CO)Cl_3$ (where Bu=n-butyl).

In the examples mentioned, Pd has been specified as platinum metal, but other platinum metals are also suitable, for example Pt, Ir, Ru or Rh. However, Pd and Rh, in particular Pd, are preferred and are present as metal, metal halide or a complex containing metal halide.

It has also been found that the platinum metal halide or the complex containing the platinum metal halide can be prepared in situ on the support during the preparation from a suitable halogen-free platinum metal compound and a halide-containing compound. Suitable halogen-free platinum metal compounds are, for example, platinum metal nitrates, acetates, propionates, butyrates, oxalates, carbonates, oxides, hydroxides, acetylacetonates and others with which those skilled in the art are familiar. Suitable halide-containing compounds are halogen-containing salts and complexes of the elements of the first to fifth main groups and the first to eighth transition groups of the Periodic Table of the Elements (Mendeleev) and also the rare earth metals (atomic numbers 58–71) and aliphatic halogenated hydrocarbons. Examples are NaBr, NaCl, $MgBr_2$, $MgCl_2$, $AlCl_3$, $CH_2Cl_2$, $NaPF_6$, $MnCl_2$, $MnBr_2$, $CoBr_2$, $CeCl_3$, $SmI_2$, $CuCl_2$, $Na_2ZnCl_4$, $TiCl_4$ and $NR_4Br$, where R is as defined above.

The amount of the platinum metal halide or that of the complex containing the platinum metal halide in the reaction-ready state is from 0.01 to 15% by weight, preferably from 0.05 to 10% by weight, calculated as the platinum metal and based on the total weight of the catalyst.

Suitable solvents for preparing supported catalysts according to the invention are, for example, water, aliphatic hydrocarbons such as pentane, n-hexane, cyclohexane, etc., aliphatic halogenated hydrocarbons such as dichloromethane, trichloromethane, etc., unsaturated hydrocarbons such as pentene, isoprene, cyclopentadiene, hexenes, hexines, cyclohexenes, cyclooctadienes, etc., aromatic hydrocarbons such as benzene, toluene, xylene, etc., halogenated aromatic hydrocarbons such as chlorobenzene, dichlorobenzene, etc., primary, secondary or tertiary alcohols such as methanol, ethanol, n-propanol, iso-propanol, n-butanol, iso-butanol, t-butanol, cumyl alcohol, iso-amyl alcohol, diethylene glycol, etc., ketones such as acetone, 2-butanone, methyl isobutyl ketone, acetylacetone, etc., ethers such as diethyl ether, diisopropyl ether, methyl t-butyl ether, dioxane, tetrahydrofuran, etc., esters such as methyl acetate, ethyl acetate, etc., nitriles such as acetonitrile, benzonitrile, etc., carbonates such as dimethyl carbonate, diethyl carbonate, diphenyl carbonate, etc., dimethylacetamide, N-methylpyrrolidinone and tetramethylurea. Of course, mixtures of such solvents can also be used.

A catalyst to be used according to the invention is prepared by methods which are basically known to those skilled in the art. Thus, solutions of one or more of the platinum metals specified and the halide-containing compounds specified can be applied, for example by soaking, adsorption, dipping, spraying, impregnation and ion exchange, to the catalyst support to be used according to the invention.

It is also possible to fix one or more platinum metals and the halide-containing compounds specified on the support by precipitation with a base. Suitable bases are, for example, alkali metal (alkaline earth metal) hydroxides such as $Ca(OH)_2$, $Mg(OH)_2$, NaOH, LiOH and KOH, alkali metal (alkaline earth metal) hydrogen carbonates such as $Ca(HCO_3)_2$, $Mg(HCO_3)_2$, $NaHCO_3$, $LiHCO_3$ and $KHCO_3$, alkali metal (alkaline earth metal) carbonates such as $CaCO_3$, $MgCO_3$, $Na_2CO_3$, $Li_2CO_3$ and $K_2CO_3$, alkali metal salts of weak organic acids such as sodium acetate, potassium acetate and lithium acetate, and alkali metal (alkaline earth metal) salts of substituted or unsubstituted phenols (in the case of substituted phenols, these are those as are described further below as being usable in the process for preparing diaryl carbonate) such as lithium phenoxide, sodium phenoxide, sodium cresoxide and potassium phenoxide. The platinum metal and the halide-containing compound can be applied to the support either successively in any order or simultaneously. A specific embodiment of the invention comprises the application of the platinum metal by precipitation of a platinum metal halide or a platinum metal halide complex with a suitable base (suitable bases are those as are described above), reduction of the precipitated platinum metal base to the metal using a suitable reducing agent such as, for example, hydrazine, formaldehyde, sodium formate, $NaBH_4$ at temperatures between 0° C. and 200° C. or gaseous hydrogen at temperatures between 0° C. and 500° C., preferably between 20 and 300° C., particularly preferably from 30 to 250° C., and reaction of the platinum metal with hydrogen halide or gaseous halogen at temperatures between 20° C. and 600° C., preferably between 50 and 500° C.

The amount of platinum metal in the solution for preparing supported catalysts of the invention is not subject to restriction, but is preferably such that the concentration of the metal in the solution is from 0.001 to 30% by weight, particularly preferably from 0.01 to 20% by weight.

The temperature of the solution before and during the reaction can be freely selected between the melting point and boiling point of the solution in question. Preference is given to working at room temperature. However, it can be advantageous to heat the solution before and/or during the reaction so as to increase the solubility of the platinum metal compound.

During the application of the solution containing the platinum metal and the solution containing the halide to the catalyst support to be used according to the invention, the mixture can be stirred. However, it can also be advantageous to allow the mixture to stand or to shake it, so that shaped bodies, if used, are not damaged by a stirrer.

After application of platinum metal and halide-containing compound to the catalyst support to be used according to the invention, the supported catalyst is separated off, for example, by filtration, sedimentation or centrifugation. In a further embodiment of the invention, the solvent is separated off by distillation.

After separating off the solvent, the supported catalysts thus obtained are dried. This can be carried out in air, in vacuo or in a stream of gas. Suitable gases for drying the supported catalyst in a stream of gas are nitrogen, oxygen, carbon dioxide and noble gases and also any mixtures of the gases specified, preferably, for example, air. Likewise suitable are gaseous alkenes such as ethene, propene, butene, butadiene and alkines such as ethine, propine, etc., in any composition.

Drying is carried out at from 20 to 200° C., preferably at from 40 to 180° C., particularly preferably at from 60 to 150° C. The drying time depends, for example, on the porosity of the support used and on the solvent used. It is generally a few hours, for example from 0.5 to 50 hours, preferably from 1 to 40 hours, particularly preferably from 1 to 30 hours.

After drying, the dried supported catalysts can be calcined. This can be carried out in air, in vacuo or in a stream of gas. Suitable gases for calcination of the supported catalyst in a stream of gas are, for example, nitrogen, oxygen, carbon dioxide or noble gases and also any mixtures of the gases specified, preferably, for example, air. Calcination is carried out at from 100 to 800° C., preferably at from 100 to 700° C., particularly preferably at from 100 to 600° C. During calcination it may be advantageous for the composition of the gas to be changed abruptly, e.g. by increasing the $O_2$ content of the calcination gas from 10 to 20% by volume after 10 hours, or continuously by, for example, increasing the oxygen content of the calcination gas from 0 to 20% by volume over a period of 20 hours at a rate of 1%/h. The calcination time is generally a few hours, for example from 0.5 to 50 hours, preferably from 1 to 40 hours, particularly preferably from 1 to 30 hours.

The aromatic hydroxy compounds which can be reacted using the supported catalysts of the invention are, for example, phenol, o-, m- or p-cresol, o-, m- or p-chlorophenol, o-, m- or p-ethylphenol, o-, m- or p-propylphenol, o-, m- or p-methoxyphenol, 2,6-dimethylphenol, 2,4-dimethylphenol, 3,4-dimethylphenol, 1-naphthol, 2-naphthol and bisphenol A, preferably phenol. If the aromatic hydroxy compound is substituted, there are generally 1 or 2 substituents which are $C_1$–$C_4$-alkyl, $C_1$–$C_4$-alkoxy, fluorine, chlorine or bromine.

For the process of the invention, any organic or inorganic bases or mixtures thereof can be used. Examples of inorganic bases which may be mentioned are, without restricting the process of the invention, alkali metal hydroxides and carbonates, carboxylates or other salts of weak acids and also alkali metal salts of aromatic hydroxy compounds of the formula (II), e.g. alkali metal phenoxides. Of course, it is also possible to use the hydrates of alkali metal phenoxides in the process of the invention. An example of such a hydrate which may be mentioned here, without restricting the process of the invention, is sodium phenoxide trihydrate. However, the amount of water added is preferably such that a maximum of 5 mol of water are used per mol of base. Higher water concentrations lead, inter alia, to poorer conversions and decomposition of the carbonates formed. Organic bases which may be mentioned, without restricting the process of the invention, are tertiary amines which can bear $C_6$–$C_{10}$-aryl, $C_7$–$C_{12}$-aralkyl and/or $C_1$–$C_{20}$-alkyl radicals as organic radicals or are pyridine bases or hydrogenated pyridine bases, for example triethylamine, tripropylamine, tributylamine, trioctylamine, benzyldimethylamine, dioctylbenzylamine, dimethylphenethylamine, 1-dimethylamino-2-phenylpropane, pyridine, N-methylpiperidine, 1,2,2,6,6-pentamethylpiperidine. The base used is preferably an alkali metal salt of an aromatic hydroxy compound, particularly preferably an alkali metal salt of the aromatic hydroxy compound (II) which is also to be reacted to form the organic carbonate. These alkali metal salts can be lithium, sodium, potassium, rubidium or caesium salts. Preference is given to using lithium, sodium and potassium phenoxide, particularly preferably sodium phenoxide.

The base can be added to the reaction mixture as a pure compound in solid form or as a melt. In a further embodiment of the invention, the base is added to the reaction mixture as a solution containing from 0.1 to 80% by weight, preferably from 0.5 to 65% by weight, particularly preferably from 1 to 50% by weight, of the base. Solvents which can be used here are alcohols or phenols, such as the phenol (II) to be reacted, or inert solvents. Examples which may be mentioned are those mentioned further below as reaction media. These solvents can be used alone or in any combination with one another. Thus, an embodiment of the process of the invention comprises, for example, dissolving the base in a phenol melt which has been diluted with a solvent. The base is preferably dissolved in the melt of an aromatic hydroxy compound, particularly preferably in a melt of the aromatic hydroxy compound (II) which is to be reacted to form the organic carbonate. Very particularly preferably, the base is added in solution in phenol. The base is added in an amount which is independent of the stoichiometry. The ratio of the platinum metal, e.g. palladium, to the base is preferably selected such that from 0.1 to 500, preferably from 0.3 to 200, particularly preferably from 0.9 to 130, equivalents of base are used per mol of platinum metal, e.g. palladium.

The process of the invention is preferably carried out without solvent. Of course, inert solvents can also be used. Examples of solvents which may be mentioned are dimethylacetamide, N-methylpyrrolidinone, dioxane, t-butanol, cumyl alcohol, iso-amyl alcohol, tetramethylurea, diethylene glycol, halogenated hydrocarbons (e.g. chlorobenzene or dichlorobenzene) and ethers.

The quaternary salts used for the purposes of the present invention can be, for example, ammonium or phosphonium salts substituted by organic radicals. Suitable salts for use in the process of the invention are ammonium and phosphonium salts which bear $C_6$–$C_{10}$-aryl, $C_7$–$C_{12}$-aralkyl and/or $C_1$–$C_{20}$-alkyl radicals as organic radicals and a halide, tetrafluoroborate or hexafluorophosphate as anion. In the process of the invention, preference is given to ammonium salts which bear $C_6$–$C_{10}$-aryl, $C_7$–$C_{12}$-aralkyl and/or $C_1$–$C_{20}$-alkyl radicals as organic radicals and a halide as anion, particular preference being given to tetrabutylammonium bromide. The amount of such a quaternary salt is from 0.1 to 50% by weight, based on the weight of the reaction mixture. This amount is preferably from 0.5 to 15% by weight, particularly preferably from 1 to 5% by weight.

The process of the invention is, preferably without solvent, carried out at from 30 to 200° C., preferably at from 30 to 150° C., particularly preferably at from 40 to 120° C., and at a pressure of from 1 to 150 bar, preferably from 2 to 50 bar, particularly preferably at from 5 to 25 bar.

The supported catalysts can be used as powders or shaped bodies and can be separated again from the reaction mixture, for example by filtration, sedimentation or centrifugation.

The preparation of aromatic carbonates using the supported platinum metal catalysts of the invention can be performed by means of different process variants. One possibility is a batchwise procedure. In the case of a continuous method in countercurrent or cocurrent or in the downflow mode over a fixed bed catalyst, space velocities of from 0.01 to 20 g of aromatic hydroxy compound per gram of supported catalyst and hour, preferably from 0.05 to 10 g of aromatic hydroxy compound per gram of supported catalyst and hour, particularly preferably from 0.1 to 5 g of aromatic hydroxy compound per gram of supported catalyst and hour, are set. The supported catalysts used in batchwise experiments can be repeatedly used for the same starting materials without purification. In the case of a continuous procedure, the supported catalysts used can remain in the reactor for a long time. Preferably, the supported catalysts of the invention are used in a continuous procedure in an individual reactor or in a cascade of reactors.

If the supported catalyst is used as a powder, the stirred vessels to be used are fitted with stirrers suitable for mixing the reaction components. When working with supported catalyst powders in suspension in stirred vessels or bubble columns, amounts of from 0.001 to 50% by weight, preferably from 0.01 to 20% by weight, particularly preferably from 0.1 to 10% by weight, of supported catalyst powder are used, based on the amount of aromatic hydroxy compound used.

In particularly preferred embodiments, the heterogeneous supported catalyst is used as a shaped body in a fixed position in stirred vessels, bubble columns, a downflow reactor or cascades of these reactors. Separation of the supported catalyst is then completely unnecessary.

EXAMPLE 1 a) Preparation of a Pulverulent Manganese Oxide Support 85 g of sodium hydroxide (2.125 mol) dissolved in 200 ml of water were added dropwise to a solution of 126 g of manganese(II) chloride (1 mol) in 500 ml of water. The precipitate thus obtained was filtered off with suction, washed and dried. It was subsequently heat treated for 3 hours at 300° C. and 2 hours at 500° C.

b) Application of Palladium to the Pulverulent Manganese Oxide 300 ml of a solution of 50 g of sodium tetrachloropalladate(II) in water containing 15% of palladium were added at room temperature to a slurry of 292.5 g of manganese oxide powder in 1500 ml of water. The slurry was subsequently made alkaline using dilute sodium hydroxide solution. The suspended solid was filtered off with suction and dried at 100° C. The catalyst contained 2.5% by weight of Pd on manganese oxide support, calculated as metal.

c) Use of the Supported Catalyst for Preparing Diphenyl Carbonate

In an autoclave (1 l) fitted with gas-introduction stirrer, condenser and downstream cold trap, 8.31 g of tetrabutylammonium bromide (TBAB) and 0.77 g of manganese(II) acetylacetonate (Mn(acac)$_2$) were dissolved in 450 g of phenol at 80° C. 4 g of the above-described supported catalyst and 2.21 g of sodium phenoxide dissolved in 50 g of phenol were then added. The pressure was then set to 10 bar while passing in a gas mixture of carbon monoxide and oxygen (95:5% by volume). The amount of gas mixture was set to 300 standard l/h. Every hour, a sample was taken from the reaction mixture and analysed by gas chromatography. The analyses indicated that the reaction mixture contained 6.6% of diphenyl carbonate after one hour, 12.7% of diphenyl carbonate after 2 hours and 16.9% of diphenyl carbonate after 3 hours. 13.6 g of a phenol/water mixture had condensed in the cold trap. The selectivity based on phenol was greater than 99%.

EXAMPLE 2 a) Preparation of Cerium/Manganese Oxide Pellets 890 g of sodium hydroxide dissolved in 6 l of water were added at 85° C. to a solution of 997.1 g of cerium(III) chloride heptahydrate (2.68 mol) and 1351 g of manganese (II) chloride tetrahydrate (6.8 mol) in 17.5 l of water. The precipitate was filtered off with suction, washed, dried at 110° C. and heat treated for 6 hours at 300° C. The milled support was mixed with 4% of graphite and pressed into pellets.

b) Application of Palladium to the Cerium/Manganese Oxide Pellets 200 ml of cerium/manganese oxide pellets were impregnated with 72.5 ml of a solution of 33.3 g of sodium tetrachloropalladate(II) in water containing 15% of palladium. The pellets were subsequently dried in air at 110° C. The catalyst contained 25 g of Pd per liter, calculated as metal.

c) Use of the Supported Catalyst for Preparing Diphenyl Carbonate

The activity test was carried out in a similar manner to Example 1, except that the catalyst was used in a fixed position in a wire mesh basket. Every hour, a sample of the reaction mixture was taken and analysed by gas chromatography. The analyses indicated that the reaction mixture contained 3.7% of diphenyl carbonate after one hour, 8.1% of diphenyl carbonate after 2 hours and 11.0% of diphenyl carbonate after 3 hours. 9.7 g of a phenol/water mixture had condensed in the cold trap. The selectivity based on phenol was greater than 99%.

EXAMPLE 3 a) Preparation of Extrudates from a Pulverulent Rare Earth Oxide Mixture

A commercially available mixture of rare earth oxides (Rhône-Poulenc) was mixed into a paste with water, extruded, dried for 5 hours at 110° C. and calcined for 5 hours at 400° C.

b) Application of Palladium to the Rare Earth Oxide Extrudates 200 ml of rare earth oxide extrudate were impregnated with 70 ml of a solution of 33.3 g of sodium tetrachloropalladate(II) in water containing 15% of palladium. The extrudates were subsequently dried in air at 110° C. The catalyst contained 25 g of Pd per liter, calculated as metal.

c) Use of the Supported Catalyst for Preparing Diphenyl Carbonate

The use of the supported catalyst for preparing diphenyl carbonate was carried out as in Example 2. Every hour, a sample was taken from the reaction mixture and analysed by gas chromatography. The analyses indicated that the reaction mixture contained 3.4% of diphenyl carbonate after one hour, 7.5% of diphenyl carbonate after 2 hours and 10.1% of diphenyl carbonate after 3 hours. 9.2 g of a phenol/water mixture had condensed in the cold trap. The selectivity based on phenol was still greater than 99%.

EXAMPLE 4 a) Application of Rhodium to the Extrudates from Example 3

200 ml of rare earth oxide extrudates were impregnated with 70 ml of a solution of 12.94 g of rhodium(III) chloride hydrate in water. The extrudates were subsequently dried in air at 110° C. The catalyst contained 25 g of Rh per liter, calculated as metal.

b) Use of the Supported Catalyst for Preparing Diphenyl Carbonate

The use of the supported catalyst for preparing diphenyl carbonate was carried out as in Example 2. Every hour, a sample was taken from the reaction mixture and analysed by gas chromatography. The analyses indicated that the reaction mixture contained 1.1% of diphenyl carbonate after one hour, 2.4% of diphenyl carbonate after 2 hours and 3.1% of diphenyl carbonate after 3 hours. 3.0 g of a phenol/water mixture had condensed in the cold trap.

EXAMPLE 5 a) Application of Palladium to the Extrudates from Example 3

200 ml of rare earth oxide extrudates were impregnated with 70 ml of a solution of 12.20 g of bis(acetonitrile) palladium(II) chloride in acetonitrile. The catalyst was subsequently dried for 5 hours at 1 mbar and 40° C. The catalyst contained 25 g of Pd per liter, calculated as metal.

b) Use of the Supported Catalyst for Preparing Diphenyl Carbonate

In a Hastelloy C4 reactor (h=100 cm, $d_i$=1.5 cm) provided with an oil-heated heating jacket, 40 ml of the catalyst prepared above were placed on a frit (about 10 cm above the lower end of the reactor) and the reactor was filled with 80 ml of inert packing (3×3 mm). The reactor was provided with a metered addition facility for gas, three metered addition facilities for liquid, a continuous liquid discharge and a pressure maintenance device on the off-gas side. The off-gas leaving the reactor continuously at its upper end ran through a three-stage condensation unit before going via an $O_2$ sensor into the off-gas line. By means of three pumps, phenolic solutions of TBAB, Mn(acac)$_3$ and sodium phenoxide (NaOPh) were metered in just above the inert packing in such a way that 100 g/h of phenol, 1.7 g/h of TBAB, 0.21 g/h of Mn(acac)$_3$ and 0.44 g/h of NaOPh flowed through the reactor. Below the catalyst bed, 150 standard l/h of CO/$O_2$ mixture containing 95% by volume of CO and 5% by volume of $O_2$ were metered in in countercurrent to the liquid phase. The reactor temperature was 90° C. and the pressure was 12 bar. Samples were taken every hour from the liquid reaction product flowing out continuously. After 4 hours, the composition of the reaction product flowing out no longer changed. The DPC content was 11.5%. Here as in the previous examples, the DPC selectivity was greater than 99%. 16 g/h of a phenol/water mixture were carried out by the reaction gas.

EXAMPLE 6 a) Application of Palladium to Cerium Dioxide Powder 25 g of cerium dioxide powder (Strem, No. 93-5816) were added at room temperature to a solution of 2.28 g (2.5 mmol) of bis(tetrabutylammonium) tetrabromopalladate in 500 ml of analytical reagent dichloromethane. The mixture was then stirred for 5 hours and filtered with suction. The supported catalyst thus obtained was dried at 50° C. in vacuo (30 mbar) for 17 hours. Determination of the palladium content by atomic absorption spectroscopy indicated that the supported catalyst contained 1.0% by weight of palladium (calculated as metal).

b) Use of the Supported Catalyst for Preparing Diphenyl Carbonate

The use of the supported catalyst for preparing diphenyl carbonate was as in Example 1. The analyses indicated that the reaction mixture contained 6.1% of diphenyl carbonate after one hour, 11.8% of diphenyl carbonate after 2 hours and 15.5% of diphenyl carbonate after 3 hours. 12.8 g of a phenol/water mixture had condensed in the cold trap. The selectivity based on phenol was greater than 99%.

EXAMPLE 7 a) Application of Palladium to Titanium Dioxide Powder

The preparation of the supported catalyst was carried out as in Example 6, except that 25 g of titanium dioxide (Riedel) were used as support. Determination of the palladium content by atomic absorption spectroscopy indicated that the supported catalyst contained 0.96% by weight of palladium (calculated as metal).

b) Use of the Supported Catalyst for Preparing Diphenyl Carbonate

The use of the supported catalyst for preparing diphenyl carbonate was carried out as in Example 1, but 6.0 g of supported catalyst were used. The analyses indicated that the reaction mixture contained 7.3% of diphenyl carbonate after one hour, 12.9% of diphenyl carbonate after 2 hours and 18.0% of diphenyl carbonate after 3 hours. 13.0 g of a phenol/water mixture had condensed in the cold trap.

EXAMPLE 8 a) Application of Palladium to Dysprosium Oxide Powder

The preparation of the supported catalyst was carried out as in Example 6, except that 25 g of dysprosium oxide (Strem, No. 93-6615) were used as support. Determination of the palladium content by atomic absorption spectroscopy indicated that the supported catalyst contained 0.92% by weight of palladium (calculated as metal).

b) Use of the Supported Catalyst for Preparing Diphenyl Carbonate

The use of the supported catalyst for preparing diphenyl carbonate was carried out as in Example 1. The analyses indicated that the reaction mixture contained 5.4% of diphenyl carbonate after one hour, 10.6% of diphenyl carbonate after 2 hours and 14.2% of diphenyl carbonate after 3 hours. 11.8 g of a phenol/water mixture had condensed in the cold trap.

EXAMPLE 9

Use of the Supported Catalyst from Example 7 for Preparing Dicresyl Carbonate

The preparation of the aromatic carbonate was carried out as in Example 7b, but para-cresol was used instead of phenol as aromatic hydroxy compound. The analyses indicated that the reaction mixture contained 4.8% of di-p-cresyl carbonate after one hour, 10.8% of di-p-cresyl carbonate after 2 hours and 14.9% of di-p-cresyl carbonate after 3 hours. 10.2 g of a p-cresol/water mixture had condensed in the cold trap.

EXAMPLE 10 a) Application of Palladium to Titanium Dioxide Powder

The preparation of the supported catalyst was carried out as in Example 7, except that the 25 g of titanium dioxide used as support were Baytitan from Bayer AG. Determination of the palladium content by atomic absorption spectroscopy indicated that the supported catalyst contained 0.98% by weight of palladium (calculated as metal).

b) Use of the Supported Catalyst for Preparing Diphenyl Carbonate

The use of the supported catalyst for preparing diphenyl carbonate was carried out as in Example 1, but 5.9 g of supported catalyst were used. The analyses indicated that the reaction mixture contained 8.6% of diphenyl carbonate after one hour, 14.4% of diphenyl carbonate after 2 hours and 19.2% of diphenyl carbonate after 3 hours. 13.9 g of a phenol/water mixture had condensed in the cold trap.

COMPARATIVE EXAMPLE 1

Use of the Supported Catalyst 5% Pd/C (Aldrich No. 20-568-0) for Preparing Diphenyl Carbonate The use of the supported catalyst for preparing diphenyl carbonate was as in Example 1. The analyses indicated that the reaction mixture contained 1.6% of diphenyl carbonate after one hour, 2.8% of diphenyl carbonate after 2 hours and 3.1% of diphenyl carbonate after 3 hours. 4.0 g of a phenol/water mixture had condensed in the cold trap.

COMPARATIVE EXAMPLE 2

Use of the Supported Catalyst 5% Pd/$Al_2O_3$ (Aldrich No. 37-148-3) for Preparing Diphenyl Carbonate The use of the supported catalyst for preparing diphenyl carbonate was as in Comparative Example 1. The analyses indicated that the reaction mixture contained 1.4% of diphenyl carbonate after one hour, 2.2% of diphenyl carbonate after 2 hours and 2.8% of diphenyl carbonate after 3 hours. 3.8 g of a phenol/water mixture had condensed in the cold trap.

What is claimed is:

1. A supported catalyst containing, in the reaction-ready state, a platinum metal, a platinum metal compound or a complex containing a platinum metal compound in an amount of from 0.01 to 15% by weight, calculated as the platinum metal and based on the total weight of the catalyst, on a support comprising one or more oxides of the metals Ti, V, Mn, Cr, Fe, Co, Ni, Cu, La, Nb, Mo, Pb, the rare earth metals having the atomic numbers from 58 to 71 and the actinides having the atomic numbers 89 to 92.

2. The catalyst of claim 1, containing 0.05 to 10% by weight of the platinum metal, based on the total weight of the catalyst.

3. The catalyst of claim 1, the support of which comprises one or more oxides of the metals Ti, V, Mn, Cr, Fe, Co, Ni, Cu, La, Nb, Mo, Pb, Ce, Pr, Nd, Sm, Eu, Gd, Tb, Dy, Ho, Er, Tm, Yb, Lu and U.

4. The catalyst of claim 1, wherein the platinum metal is Pd or Rh, present as metal, metal halide or a complex containing metal halide.

5. The catalyst of claim 4, wherein the platinum metal is Pd.

6. The catalyst of claim 3, wherein the catalyst support used comprises one or more metal oxides from the group V, Mn, Ti, Co, Cu, La, the rare earth metals (atomic numbers 58–71), either as chemically uniform pure substances or as mixtures.

7. The catalyst of claim 1, which can be prepared by joint or successive application of a platinum metal compound and a compound acting as cocatalyst to a support, wherein the platinum metal compound used is a platinum metal halide or a platinum metal halide complex or the platinum metal halide or the platinum metal halide complex is formed on the catalyst support from a halide-free platinum metal compound and a halide-containing compound or is formed on the catalyst support from a halide-free platinum metal compound by reaction with a reducing agent at from 0 to 500° C. to first give the elemental platinum metal which is subsequently further reacted with gaseous hydrogen halide or gaseous halogen at from 20 to 600° C.

8. The catalyst of claim 7, wherein platinum metal halides or complexes containing platinum metal halides and nitriles, CO, olefins, amines, phosphines, water or further halide are used or are produced on the support by joint or successive application of a platinum metal compound from the group of acetates, nitrates, acetylacetonates, oxalates and hydroxides and a halogen-containing compound from the group NaCl, NaBr, $MgCl_2$, $MgBr_2$, $MnCl_2$, $MnBr_2$, $CuCl_2$ and tetrabutylammonium bromide.

9. The catalyst of claim 7, wherein the compound acting as cocatalyst is applied using a halide, oxide, carboxylate of a $C_2$–$C_6$-carboxylic acid, diketonate, nitrate or a complex, which can contain CO, olefins, amines, nitriles, phosphines or halide, of a metal acting as cocatalyst.

10. In the preparation of an aromatic carbonate of the formula

R—O—COO—R, where

R is substituted or unsubstituted $C_6$–$C_{12}$-aryl,
by reaction of an aromatic hydroxy compound of the formula

R—OH, where

R is as defined above, with carbon monoxide and oxygen in the presence of a cocatalyst, a quaternary ammonium or phosphonium salt and a base at from 30 to 200° C. and at a pressure of from 1 to 150 bar, and in the presence of a catalyst, the improvement wherein the catalyst comprises a supported catalyst according to claim 1.

11. The process of claim 10, wherein the supported catalyst is, in a continuous method in countercurrent or cocurrent or in the downflow mode over a fixed-bed catalyst, exposed to from 0.01 to 20 g of aromatic hydroxy compound per gram of supported catalyst and hour, and when working in suspension in stirred vessels or bubble columns, the supported catalyst is used in amounts of from 0.001 to 50% by weight, based on the amount of aromatic hydroxy compound used.

12. The process of claim 11, wherein, when a fixed-bed catalyst is used, the catalyst is exposed to from 0.05 to 10 g of aromatic hydroxy compound per gram of catalyst and hour.

13. The process of claim 12, wherein, when a fixed-bed catalyst is used, the catalyst is exposed to from 0.1 to 5 g of aromatic hydroxy compound per gram of catalyst and hour.

14. The process of claim 11, wherein, when a suspended catalyst is used, the catalyst is used in an amount of from 0.01 to 20% by weight, based on the amount of aromatic hydroxy compound used.

15. The process of claim 14, wherein, when a suspended catalyst is used, the catalyst is used in an amount of from 0.1 to 10% by weight, based on the amount of aromatic hydroxy compound used.

16. The process of claim 10, wherein the base used is a tertiary amine, alkali metal phenoxide or alkali metal salt of a weak acid.

17. The process of claim 10, wherein the quaternary salt used is a tetraalkylammonium or tetraalkylphosphonium salt.

18. The process of claim 10, which is carried out at from 30 to 150° C.

19. The process of claim 18, which is carried out at from 40 to 120° C.

20. The process of claim 10, which is carried out at from 2 to 50 bar.

* * * * *